(12) United States Patent
Yoon et al.

(10) Patent No.: US 8,232,370 B2
(45) Date of Patent: Jul. 31, 2012

(54) **ANTIMICROBIAL PROTEIN SPECIFIC TO *STAPHYLOCOCCUS AUREUS***

(75) Inventors: Seongjun Yoon, Seoul (KR); Sanghyeon Kang, Seoul (KR); Seabong Kyoung, Sungnam-Si (KR); Yunjaie Choi, Seoul (KR); Jeesoo Son, Seoul (KR)

(73) Assignee: Intron Biotechnology, Inc. (KR)

( * ) Notice: Subject to any disclaimer, the term of this patent is extended or adjusted under 35 U.S.C. 154(b) by 490 days.

(21) Appl. No.: 12/308,627

(22) PCT Filed: Jul. 27, 2007

(86) PCT No.: PCT/KR2007/003629
§ 371 (c)(1),
(2), (4) Date: Jun. 15, 2009

(87) PCT Pub. No.: WO2008/016240
PCT Pub. Date: Feb. 7, 2008

(65) Prior Publication Data
US 2010/0144619 A1    Jun. 10, 2010

(30) Foreign Application Priority Data
Aug. 4, 2006 (KR) .................. 10-2006-0073562

(51) Int. Cl.
*A61K 38/16* (2006.01)
*C07K 14/195* (2006.01)
(52) U.S. Cl. .................. 530/350; 514/2.4; 536/23.7
(58) Field of Classification Search .................. None
See application file for complete search history.

(56) References Cited

U.S. PATENT DOCUMENTS

| | | | |
|---|---|---|---|
| 6,056,954 A | 5/2000 | Fischetti | 424/94.1 |
| 6,056,955 A | 5/2000 | Fischetti | 424/94.1 |
| 6,121,036 A | 9/2000 | Ghanbari | 436/69.3 |
| 6,264,945 B1 | 7/2001 | Fischetti | 424/94.1 |
| 6,432,444 B1 | 8/2002 | Fischetti et al. | 424/443 |
| 7,572,602 B1 * | 8/2009 | Donovan | 435/69.7 |
| 7,582,291 B2 * | 9/2009 | Yoong et al. | 424/93.6 |
| 2003/0152594 A1 | 8/2003 | Pillich | 424/243.1 |
| 2003/0216338 A1 | 11/2003 | Merril | 436/235.1 |
| 2004/0091470 A1 | 5/2004 | Fischetti et al. | 424/94.6 |

(Continued)

FOREIGN PATENT DOCUMENTS
KR    2006-55461    6/2006

(Continued)

OTHER PUBLICATIONS

O'Flaherty et al, Journal of Bacteriology, vol. 186, pp. 2862-2871, 2004, Gene of *Staphylococcal phage* KL a new lineage of Myoviridae infecting gram-positive bacteria with a low G+C content.*

(Continued)

*Primary Examiner* — Albert Navarro
*Assistant Examiner* — Ginny Portner
(74) *Attorney, Agent, or Firm* — Ballard Spahr LLP

(57) ABSTRACT

The present invention relates to a novel bacteriophage-originated protein having antimicrobial activity, more precisely an antimicrobial protein originated from lytic bacteriophage having killing activity specific to *Staphylococcus aureus* which is the causing agent of infectious diseases in human and animals, a pharmaceutical composition for the prevention and treatment of the disease caused by *Staphylococcus aureus*, an antibiotic and a disinfectant containing the bacteriophage-originated antimicrobial protein as an active ingredient.

7 Claims, 8 Drawing Sheets

U.S. PATENT DOCUMENTS

| | | | |
|---|---|---|---|
| 2004/0146490 A1* | 7/2004 | Kelly et al. | 424/93.6 |
| 2005/0260171 A1 | 11/2005 | Ghanbari et al. | 424/630 |
| 2007/0025978 A1* | 2/2007 | Yoong et al. | 424/94.63 |
| 2007/0077235 A1* | 4/2007 | Loomis et al. | 424/93.6 |
| 2010/0004321 A1* | 1/2010 | Ross et al. | 514/44 R |
| 2010/0203019 A1 | 8/2010 | Yoon | 424/93.6 |
| 2010/0203180 A1 | 8/2010 | Yoon | 514/2 |
| 2010/0254950 A1 | 10/2010 | Yoon | 424/93.6 |
| 2010/0267117 A1 | 10/2010 | Yoon | 435/6 |

FOREIGN PATENT DOCUMENTS

| | | |
|---|---|---|
| KR | 2006-73562 | 8/2006 |
| KR | 2007-82358 | 8/2007 |
| KR | 100781669 | 12/2007 |
| KR | 2007-82357 | 2/2009 |
| WO | WO 03/067991 | 8/2003 |
| WO | WO 2004/020451 | 3/2004 |
| WO | WO 2004/062677 | 7/2004 |
| WO | WO 2006/063176 | 6/2006 |
| WO | WO 2007/148919 | 12/2007 |
| WO | WO 2008/016240 | 2/2008 |
| WO | WO 2009/035303 | 3/2009 |

OTHER PUBLICATIONS

Fenton et al, 2010, Bioengineered Bugs, vol. 1(6), pp. 404-497, November-December, The truncated phage lysin ChapK eliminates *Staphylococcus aureus* in the nares of mice.*

Graham, S et al, Journal of Antimicrobial Chemotherapy, 2007, vol. 59, pp. 759-762, Potent synergistic inhibition of *Staphylococcus aureus* upon exposure to a combination of the endopeptidase lysostaphin and the cationic peptide ranalexin.*

Jain, A et al, Journal of Microbiological Methods, vol. 76, pp. 88-92, 2009, Biofilm production, a marker of pathogenic potential of clonizing and commensal *Staphylococci*.*

Sass, P et al, Applied and Environmental Microbiology, Jan. 2007, pp. 347-352, vol. 73(1), Lytic Activity of Recombinat Bacteriophage 11 and 12 endolysins on whole cells and biofilms of *Staphylococcus aureus*.*

Skurnik, M et al, International Journal of Medical Microbiology, vol. 296, pp. 5-14, 2006, Phage Therapy:Facts and fiction.*

Loessner, M J, Current Opinion in Microbiology, vol. 8, pp. 480-487, 2005, Bacteriophage endolysins-current state of research and applications.*

Matsuzaki, S et al, 2003, The Journal of Infectious Diseases, vol. 187, pp. 613-624, Experimental protection of mice against Lethal *Staphyloccucus aureus* Infection by Novel Bacteriophage oMR11.*

Bernhardt TG, Wang IN, Struck DK, Young R. (2002) Breaking Free: "protein antibiotics" and phage lysis, Res Microbiol. 153(8): 493-501.

Genbank Accession No. AA047477, titled "Soares pregnant uterus NbHPU", entered Sep. 19, 1996.

Genbank Accession No. AY176327, titled "*Staphylococcus* phage K, complete genome", Direct Submisson (See O'Flaherty et al., 2004).

Genbank Accession No. AY954969, titled "Bacteriophage G1, complete genome", Direct Submisson (See Kwan et al., 2005).

Kwan T, Liu J, DuBow M, Gros P, Pelletier J. (2005) The complete genomes and proteomes of 27 *Staphylococcus aureus* bacteriophages. Proc Natl Acad Sci USA. 102(14): 5174-5179.

Loessner MJ, (2005) Bacteriophage endolysins—current state of research and applications. Curr Opin Microbiol. 8(4): 480-487.

Loessner MJ, Gaeng S, Scherer S, (1999) Evidence for a holin-like protein gene fully embedded out of frame in the endolysin gene of *Staphylococcus aureus* bacteriophage 187, J Bacteriol. 181(15): 4452-4460.

Matsuzuki S, Rashel M, Uchiyama J, Sakurai S, Ujihara T, Kuroda M, Ikeuchi M, Tani T, Fujieda M, Wakiguchi H, Imai S. (2005) Bacteriophage therapy: a revitalized therapy against bacterial infections diseases, J Infect Chemother. 11(5): 211-219.

Matsuzaki S, Yasuda M, Nishikawa H, Kuroda M, Ujihara T, Shuin T, Shen Y, Jin Z, Fujimoto S, Nashimuzzaman MD, Wakiguchi H, Sugihara S, Sugiura T, Koda S, Muraoka A, Imai S. (2003) Experimental protection of mice against lethal *Staphylococcus aureus* infection by novel bacteriophage phi MR11. J Infect Dis. 187(4): 613-624.

O'Flaherty S, Coffey A, Edwards R, Meaney W, Fitzgerald GF, Ross RP. (2004) Genome of *Staphylococcal* phage K: a new lineage of Myoviridae infecting gram-positive bacteria with low G+C Content. J Bacteriol. 186(9): 2862-2871.

Skurnik M, Strauch E. (2006) Phage therapy: facts and fiction. Int J Med Microbiol. 296(1): 5-14.

Vybiral D, Takác M, Loessner M, Witte A, von Ahsen U, Bläsi U. (2003) Complete nucleotide sequence and molecular characterization of two lytic *Staphylococcus aureus* phages: 44AHJD and P68. FEMS Microbiol Lett. 219(2): 275-283.

Yoong P, Schuch R, Nelson D, Fischetti VA. (2004) Identification of a broadly active phage lytic enzyme with lethal activity against antibiotic-resistant *Enterococcus faecalis* and *Enterococcus faecium*. J Bacteriol. 186(14): 4808-4812.

Arciola CR, Baldassarri L, Montanaro L. (2001) Presence of icaA and icaD genes and slime production in a collection of *Staphylococcal* strains from catheter-associated infections. J Clin Microbiol. 39(6): 2151-2156.

Arciola CR, Montanaro L, Baldassarri L, Borsetti E, Cavedagna D, Donati E. (1999) Slime production by *Staphylococci* isolated from prosthesis-associated infections. New Microbiol. 22(4): 337-341.

Bokarewa MI, Jin T, Tarkowski A. (2006) *Staphylococcus aureus*: *Staphylokinase*. Int J Biochem Cell Biol. 38(4): 504-509.

Cisani G, Varaldo PE, Grazi G, Soro O. (1982) High-level potentiation of lysostaphin anti-staphylococcal activity by lysozyme. Antimicrob Agents Chemother. 21(4): 531-535.

Costerton JW, Lewandowski Z, DeBeer D, Caldwell D, Korber D, James G. (1994) Biofilms, the customized microniche. J Bacteriol. 176(8): 2137-2142.

Cramton SE, Gerke C, Schnell NF, Nichols WW, Götz F. (1999) The intercellular adhesion (ica) locus is present in *Staphylococcus aureus* and is required for biofilm formation. Infect Immun. 67(10): 5427-5433.

Graham S, Coote PJ. (2007) Potent, synergistic inhibition of *Staphylococcus aureus* upon exposure to a combination of the endopeptidase lysostaphin and the cationic peptide ranalexin. J Antimicrob Chemother. 59(4): 759-762.

Gründling A, Missiakas DM, Schneewind O. (2006) *Staphylococcus aureus* mutants increased lysostaphin resistance. J Bacteriol. 188(17): 6286-6297.

Kusuma C, Jadanova A, Chanturiya T, Kokai-Kun JF. (2007) Lysostaphin-resistant variants of *Staphylococcus aureus* demonstrate reduced fitness in vitro and in vivo. Antimicrob Agents Chemother. 51(2): 475-482.

Mah TF, O'Toole GA. (2001) Mechanisms of biofilm resistance to antimicrobial agents. Trends Microbiol. 9(1): 34-39.

McKenney D, Pouliot KL, Wang Y, Murthy V, Ulrich M, Döring G, Lee JC, Goldmann DA, Pier GB. (1999) Broadly protective vaccine for *Staphylococcus aureus* based on an in vivo-expressed antigen. 284(5419): 1523-1527.

O'Gara JP, Humphreys H. (2001) *Staphylococcus epidermidis* biofilms: importance and implications. J Med Microbiol. 50(7): 582-587.

Resch A, Fehrenbacher B, Eisele K, Schaller M, Götz F. (2005) Phage release from biofilm and planktonic *Staphylococcus aureus* cells. FEMS Microbiol Lett. 252(1): 89-96.

Sass P, Bierbaum G. (2007) Lytic activity of recombinant bacteriophage phi11 and phi12 endolysins on whole cells and biofilms of *Staphylococcus aureus*. Appl Environ Microbiol. 73(1): 347-352.

Schuch R, Nelson D, Fischetti VA. (2002) A bacteriolytic agent that detects and kills *Bacillus anthracis*. Nature. 418(6900): 884-889.

Severance PJ, Kauffman CA, Sheagren JN. (1980) Rapid identification of *Staphylococcus aureus* by using lysostaphin sensitivity. J Clin Microbiol. 11(6): 724-727.

Waldvogel FA. (2000) Infections Associated with Indwelling Medical Devices, pp. 55-88, 2000, ASM, Washington, DC.

Walencka E, Sadowska B, Rózalska S, Hryniewicz W, Rózalska B. (2006) *Staphylococcus aureus* biofilm as a target for single or repeated doses of oxacillin, vancomycin, linezolid and/or lysostaphin. Folia Microbiol (Praha). 51(5): 381-386.

Wu JA, Kusuma C, Mond JJ, Kokai-Kun JF. (2003) Lysostaphin disrupts *Staphylococcus aureus* and *Staphylococcus epidermidis* biofilms on artificial surfaces. Antimicrob Agents Chemother. 47(11): 3407-3414.

International Search Report issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

Written Opinion issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

International Preliminary Report on Patentability issued Mar. 16, 2010 for WO 2009/035303 published on Mar. 19, 2009 (Application No. PCT/KR2008/005434 filed on Sep. 12, 2008) (Inventors—Yoon et al.; Applicant—Intron Biotechnology, Inc.).

International Preliminary Report on Patenability issued Dec. 22, 2008 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

International Search Report issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

Written Opinion issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).

International Preliminary Report on Patentability issued Feb. 10, 2009 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

International Search Report issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

Written Opinion issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).

Notice of Allowance with Examiner Interview Summary issued Jun. 1, 2011 for U.S. Appl. No. 12/378,457, filed Feb. 12, 2009 (Inventors—Yoon et al.).

Final Rejection issued Apr. 28, 2011 for U.S. Appl. No. 12/378,457, filed Feb. 12, 2009 (Inventors—Yoon et al.).

Response after Non-Final Office Action filed Feb. 25, 2011 for U.S. Appl. No. 12/378,457, filed Feb. 12, 2009 (Inventors—Yoon et al.).

Non-Final Rejection issued Oct. 26, 2010 for U.S. Appl. No. 12/378,457, filed Feb. 12, 2009 (Inventors—Yoon et al.).

Preliminary Amendment filed Mar. 12, 2010 for U.S. Appl. No. 12/677,990, filed Sep. 12, 2008) (Inventors—Yoon et al.).

Response to Non-Final Office Action filed Jul. 5, 2011 for U.S. Appl. No. 12/308,622, filed May 27, 2009 (Inventors—Yoon et al.).

Non-Final Office Action issued Mar. 3, 2011 for U.S. Appl. No. 12/308,622, filed May 27, 2009 (Inventors—Yoon et al.).

Preliminary Amendment filed Dec. 19, 2008 for U.S. Appl. No. 12/308,622, filed May 27, 2009 (Inventors—Yoon et al.).

\* cited by examiner

[Fig. 1]
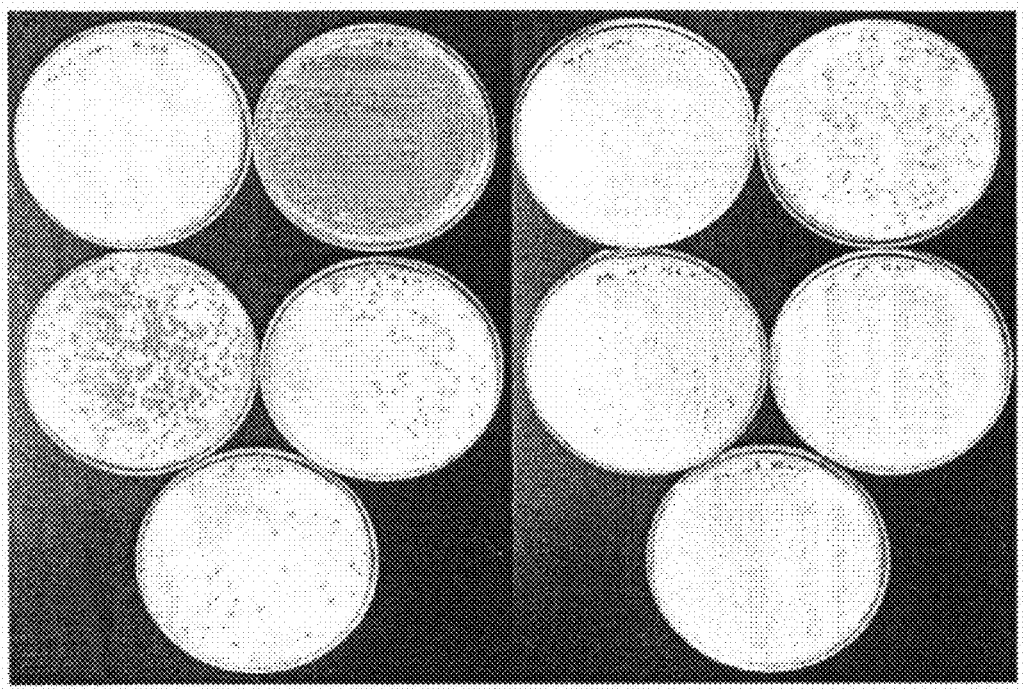
[Fig. 2]
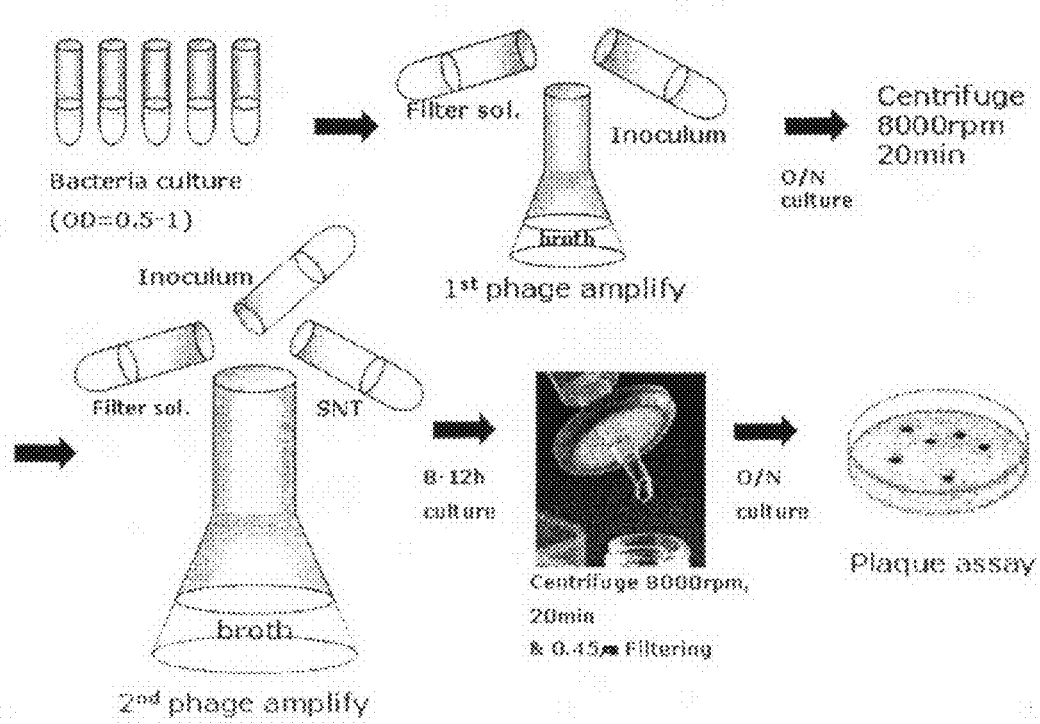

[Fig. 3]
[Fig. 4]
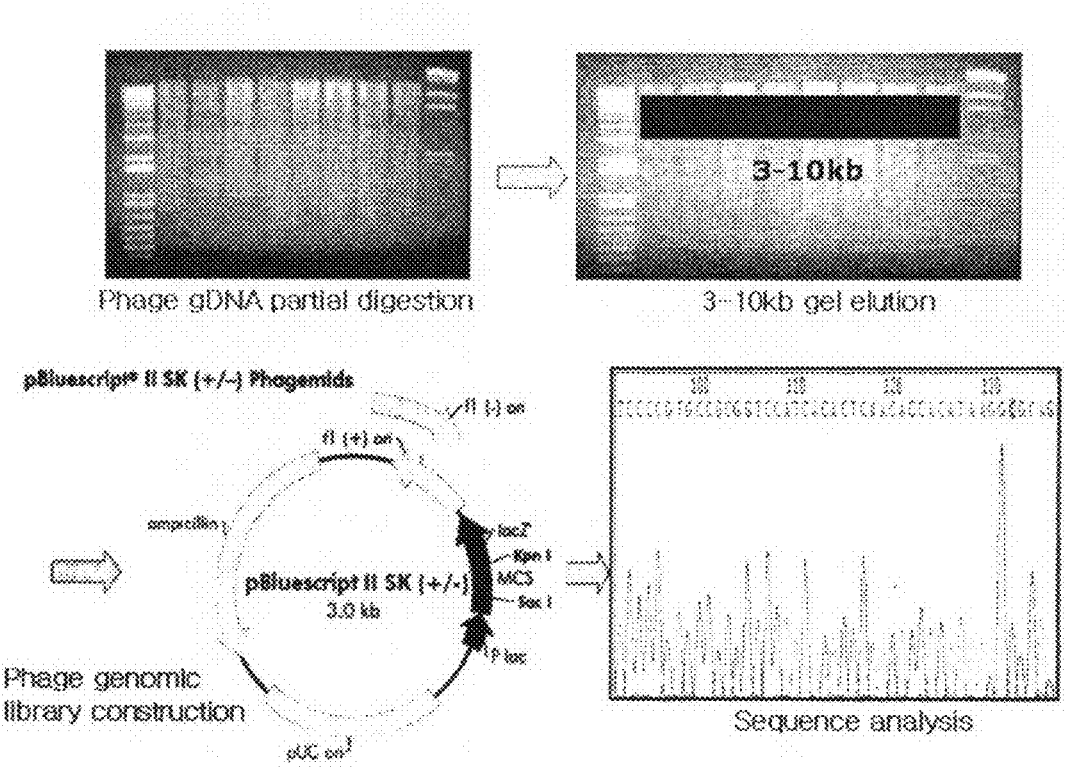

[Fig. 5]
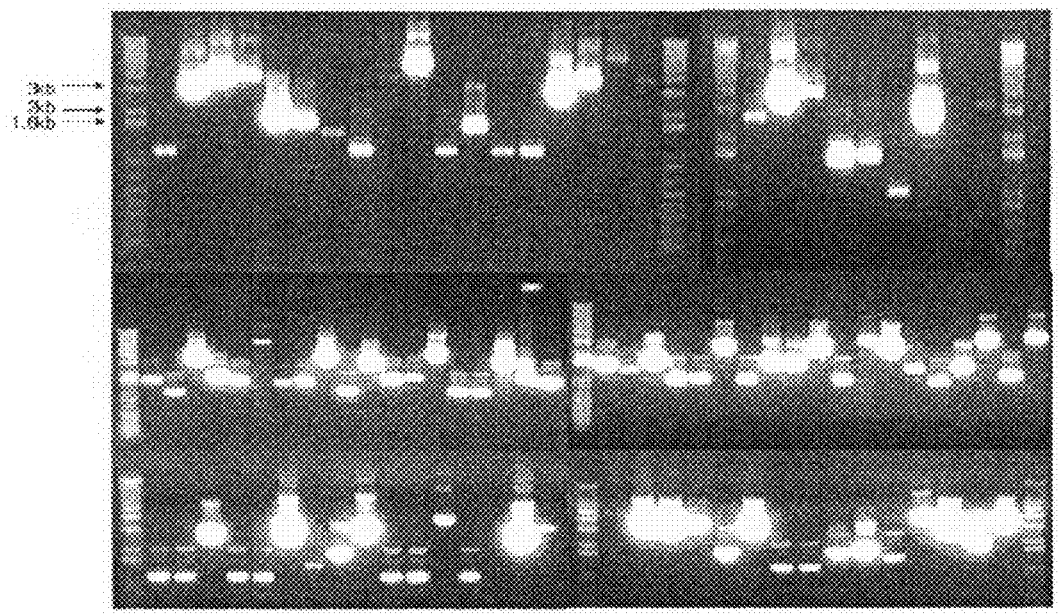
[Fig. 6]
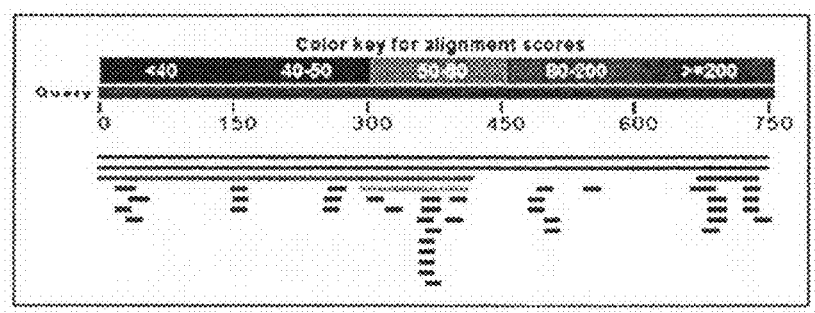

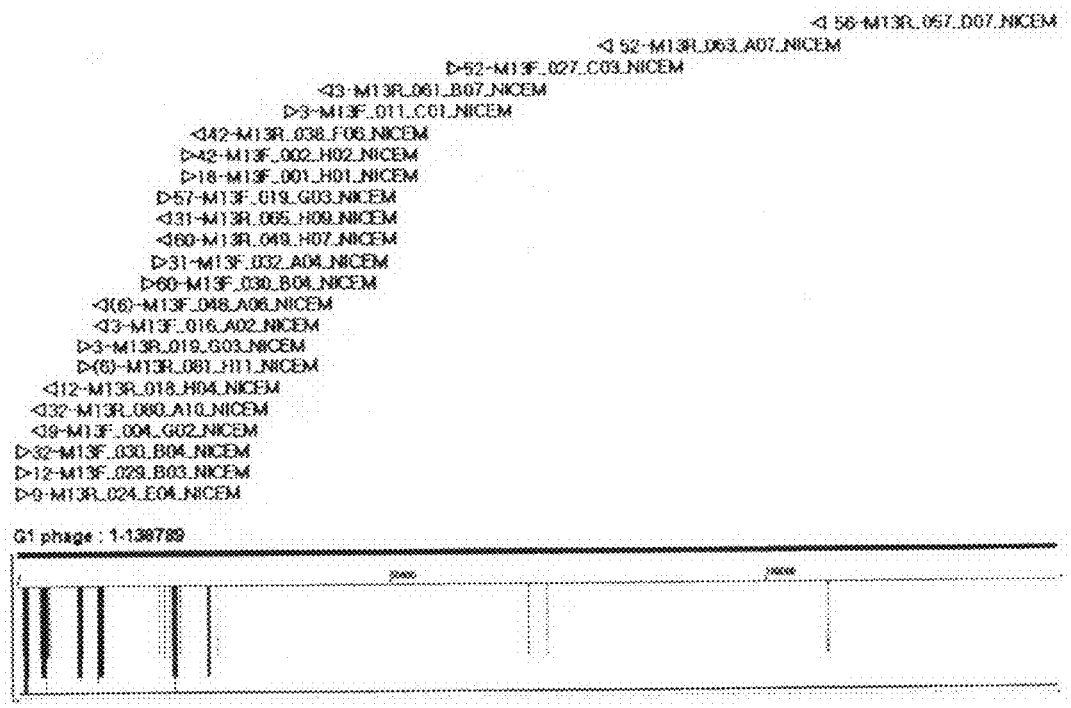
[Fig. 7]

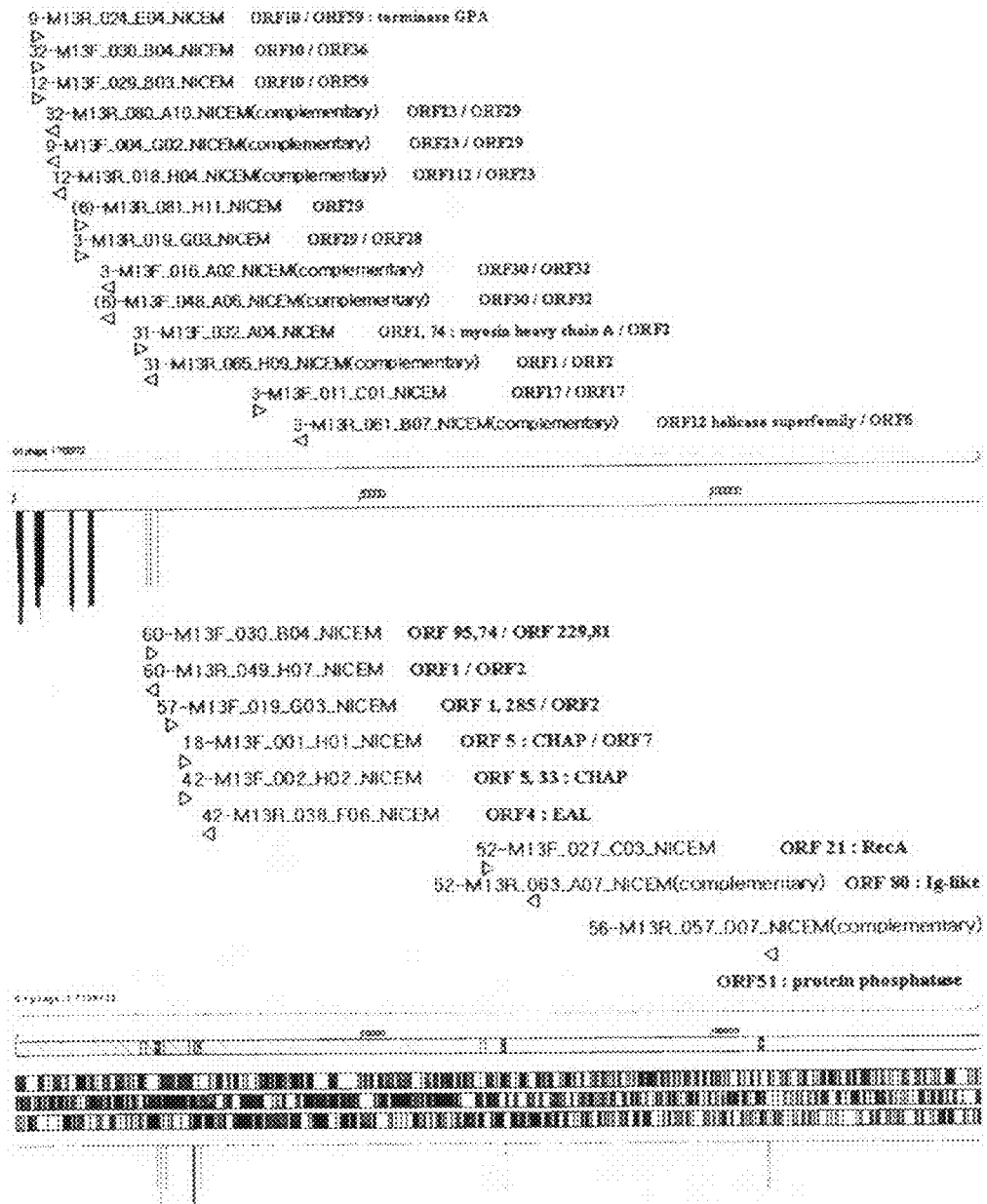
[Fig. 8]

[Fig. 11]
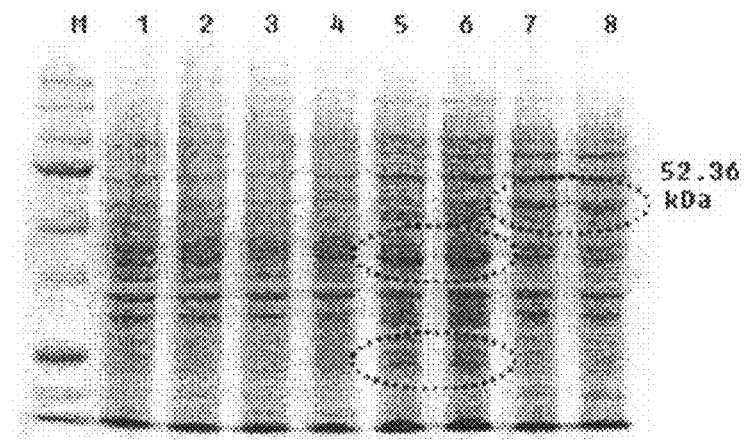
[Fig. 12]
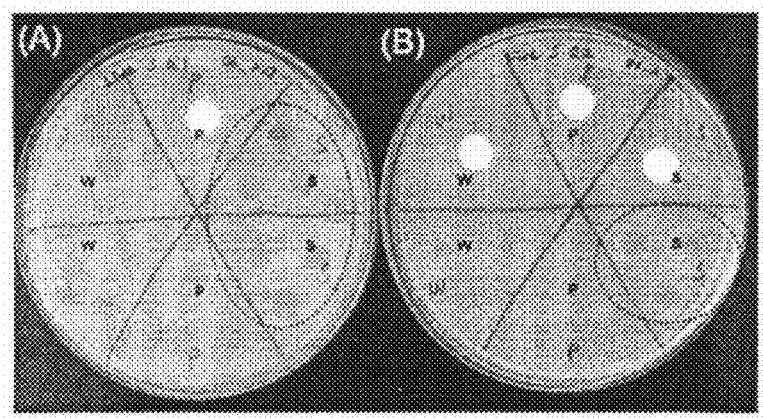
[Fig. 13]
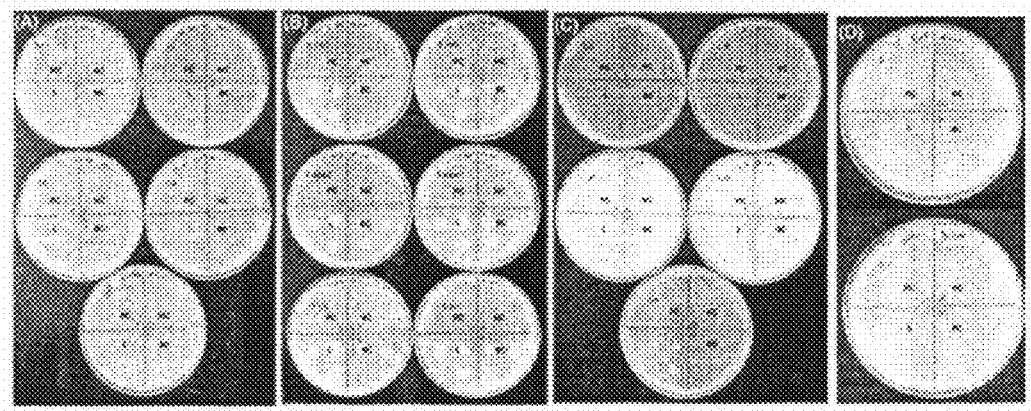

```
                              SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 1
gtcgtgactg ggaaaaccct ggcg                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 2
tcctgtgtga aattgttatc cgct                                              24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 3
ttatttaccc gtgtgccaag                                                   20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 4
gataaacatg accgacctac tg                                                22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 5
acctcgtgat agtaaagacc c                                                 21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct
```

```
<400> SEQUENCE: 6
gaggaggaag ttaagtaatg gc                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 7
gcagatggtt actatcatgc ac                                              22

<210> SEQ ID NO 8
<211> LENGTH: 801
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 8
atggctaaga ctcaagcaga aataaataaa cgtttagacg cttatgcaaa aggtacagta      60
gacagtcctt atagaattaa aaaagctaca agctatgacc catcgtttgg tgtaatggaa     120
gcaggagcaa ttgacgcaga tggttactat catgcacagt gccaagactt aattactgat     180
tatgtattat ggttaacaga taataaagtt agaacttggg gtaatgctaa agaccaaatc     240
aaacaaagtt atggtactgg atttaaaata catgaaaata aaccttctac agtacctaaa     300
aaaggatgga ttgctgtatt tacatccggt agttatcagc aatggggtca cataggtatt     360
gtatatgatg gaggtaatac ttctacattt actatttag agcaaaactg gaacggttac     420
gctaataaaa aacctacaaa acgtgtagat aattattacg gattaactca ttttattgag     480
atacctgtaa aagcaggaac tactgttaaa aaagaaacag ctaagaaaag tgcaagtaaa     540
acacctgcac ctaaaaagaa agcaacacta aaagtttcta agaaccatat taactataca     600
atggataaac gtggtaagaa acctgaagga atggtaatac acaacgatgc aggtcgttct     660
tcagggcaac aatacgagaa ttcattagct aacgcaggtt atgctagata tgctaatggt     720
attgctcatt actatggctc tgaaggttat gtatgggaag caatagatgc taagaatcaa     780
attgcttggc acacgggtaa a                                              801

<210> SEQ ID NO 9
<211> LENGTH: 267
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 9

Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
```

```
                65                  70                  75                  80
Lys Gln Ser Tyr Gly Thr Gly Phe Lys Ile His Glu Asn Lys Pro Ser
                        85                  90                  95
Thr Val Pro Lys Lys Gly Trp Ile Ala Val Phe Thr Ser Gly Ser Tyr
                100                 105                 110
Gln Gln Trp Gly His Ile Gly Ile Val Tyr Asp Gly Asn Thr Ser
            115                 120                 125
Thr Phe Thr Ile Leu Glu Gln Asn Trp Asn Gly Tyr Ala Asn Lys Lys
        130                 135                 140
Pro Thr Lys Arg Val Asp Asn Tyr Tyr Gly Leu Thr His Phe Ile Glu
145                 150                 155                 160
Ile Pro Val Lys Ala Gly Thr Thr Val Lys Lys Glu Thr Ala Lys Lys
                165                 170                 175
Ser Ala Ser Lys Thr Pro Ala Pro Lys Lys Ala Thr Leu Lys Val
                180                 185                 190
Ser Lys Asn His Ile Asn Tyr Thr Met Asp Lys Arg Gly Lys Lys Pro
                195                 200                 205
Glu Gly Met Val Ile His Asn Asp Ala Gly Arg Ser Ser Gly Gln Gln
        210                 215                 220
Tyr Glu Asn Ser Leu Ala Asn Ala Gly Tyr Ala Arg Tyr Ala Asn Gly
225                 230                 235                 240
Ile Ala His Tyr Tyr Gly Ser Glu Gly Tyr Val Trp Glu Ala Ile Asp
                245                 250                 255
Ala Lys Asn Gln Ile Ala Trp His Thr Gly Lys
                260                 265

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
ccatggctaa gactcaagca ga                                              22

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 11
gcggccgcct atttgaatac tccccagg                                        28

<210> SEQ ID NO 12
<211> LENGTH: 630
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 12
atgagtgcta gtgatgctca attccttaaa aacgaacaag cagtattcca atttactgca      60
gagaaattta agaatggggg tcttactcct aatcgtaaaa ctgtaagatt gcatatggaa     120
tttgttccaa cagcttgtcc tcatcgttct atggttcttc atacaggatt taatccagta     180
```

```
acacaaggaa gaccatctca agcaataatg aataaactaa aagattattt cattaaacaa    240
attaaaaact acatggataa aggaacttca agttctacag tagttaaaga cggtaaaaca    300
agtagcgcaa gtacaccggc aactagacca gtaacaggct cttggaaaaa gaaccagtac    360
ggaacttggt acaaaccgga aaatgcaaca tttgttaatg gtaaccaacc tatagtaact    420
agaataggtt ctccattctt aaatgctcca gtaggaggta acttaccggc aggagctaca    480
attgtatatg acgaagtttg tatccaagca ggtcacattt ggataggtta caatgcttac    540
aatggtaaca gagtatattg ccctgttaga acttgtcaag gagttccacc taatcatata    600
cctggggttg cctggggagt attcaaatag                                      630
```

<210> SEQ ID NO 13
<211> LENGTH: 209
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 13

```
Met Ser Ala Ser Asp Ala Gln Phe Leu Lys Asn Glu Gln Ala Val Phe
 1               5                  10                  15

Gln Phe Thr Ala Glu Lys Phe Lys Glu Trp Gly Leu Thr Pro Asn Arg
            20                  25                  30

Lys Thr Val Arg Leu His Met Glu Phe Val Pro Thr Ala Cys Pro His
        35                  40                  45

Arg Ser Met Val Leu His Thr Gly Phe Asn Pro Val Thr Gln Gly Arg
    50                  55                  60

Pro Ser Gln Ala Ile Met Asn Lys Leu Lys Asp Tyr Phe Ile Lys Gln
65                  70                  75                  80

Ile Lys Asn Tyr Met Asp Lys Gly Thr Ser Ser Thr Val Val Lys
                85                  90                  95

Asp Gly Lys Thr Ser Ser Ala Ser Thr Pro Ala Thr Arg Pro Val Thr
            100                 105                 110

Gly Ser Trp Lys Lys Asn Gln Tyr Gly Thr Trp Tyr Lys Pro Glu Asn
        115                 120                 125

Ala Thr Phe Val Asn Gly Asn Gln Pro Ile Val Thr Arg Ile Gly Ser
    130                 135                 140

Pro Phe Leu Asn Ala Pro Val Gly Gly Asn Leu Pro Ala Gly Ala Thr
145                 150                 155                 160

Ile Val Tyr Asp Glu Val Cys Ile Gln Ala Gly His Ile Trp Ile Gly
                165                 170                 175

Tyr Asn Ala Tyr Asn Gly Asn Arg Val Tyr Cys Pro Val Arg Thr Cys
            180                 185                 190

Gln Gly Val Pro Pro Asn His Ile Pro Gly Val Ala Trp Gly Val Phe
        195                 200                 205

Lys
```

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 14

```
ctctgaaggt tatgtatg                                                  18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 15
tttttaagga attgagca                                                  18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 16
gggaagcaat agatgcta                                                  18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 17
catacataac cttcagag                                                  18

<210> SEQ ID NO 18
<211> LENGTH: 1488
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 18
atggctaaga ctcaagcaga aataaataaa cgtttagacg cttatgcaaa aggtacagta     60
gacagtcctt atagaattaa aaaagctaca agctatgacc catcgtttgg tgtaatggaa    120
gcaggagcaa ttgacgcaga tggttactat catgcacagt gccaagactt aattactgat    180
tatgtattat ggttaacaga taataaagtt agaacttggg gtaatgctaa agaccaaatc    240
aaacaaagtt atggtactgg atttaaaata catgaaaata accttctac agtacctaaa    300 aaaggatgga ttgctgtatt tacatccggt agttatcagc aatggggtca cataggtatt    360
gtatatgatg gaggtaatac ttctacattt actattttag agcaaaactg gaacggttac    420
gctaataaaa aacctacaaa acgtgtagat aattattacg gattaactca ttttattgag    480
atacctgtaa aagcaggaac tactgttaaa aagaaacag ctaagaaaag tgcaagtaaa    540
acacctgcac ctaaaagaa agcaacacta aaagtttcta agaaccatat taactataca    600
atggataaac gtggtaagaa acctgaagga atggtaatac acaacgatgc aggtcgttct    660
tcagggcaac aatacgagaa ttcattagct aacgcaggtt atgctagata tgctaatggt    720
attgctcatt actatggctc tgaaggttat gtatgggaag caatagatgc taagaatcaa    780
attgcttggc acacaggaga tggaacagga gcaaactcag gtaactttag atttgcaggt    840
```

```
attgaagtct gtcaatcaat gagtgctagt gatgctcaat tccttaaaaa cgaacaagca    900
gtattccaat ttactgcaga gaaatttaaa gaatggggtc ttactcctaa tcgtaaaact    960
gtaagattgc atatggaatt tgttccaaca gcttgtcctc atcgttctat ggttcttcat   1020
acaggattta atccagtaac acaaggaaga ccatctcaag caataatgaa taaactaaaa   1080
gattatttca ttaaacaaat taaaaactac atggataaag gaacttcaag ttctacagta   1140
gttaaagacg gtaaaacaag tagcgcaagt acaccggcaa ctagaccagt aacaggctct   1200
tggaaaaaga accagtacgg aacttggtac aaaccggaaa atgcaacatt tgttaatggt   1260
aaccaaccta tagtaactag aataggttct ccattcttaa atgctccagt aggaggtaac   1320
ttaccggcag gagctacaat tgtatatgac gaagtttgta tccaagcagg tcacatttgg   1380
ataggttaca atgcttacaa tggtaacaga gtatattgcc ctgttagaac ttgtcaagga   1440
gttccaccta atcatatacc tggggttgcc tggggagtat tcaaatag             1488
```

<210> SEQ ID NO 19
<211> LENGTH: 495
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 19

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Gln Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255
```

Ala Lys Asn Gln Ile Ala Trp His Thr Gly Asp Gly Thr Gly Ala Asn
             260                 265                 270

Ser Gly Asn Phe Arg Phe Ala Gly Ile Glu Val Cys Gln Ser Met Ser
         275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
             325                 330                 335

Met Val Leu His Thr Gly Phe Asn Pro Val Thr Gln Gly Arg Pro Ser
         340                 345                 350

Gln Ala Ile Met Asn Lys Leu Lys Asp Tyr Phe Ile Lys Gln Ile Lys
    355                 360                 365

Asn Tyr Met Asp Lys Gly Thr Ser Ser Ser Thr Val Val Lys Asp Gly
370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
             405                 410                 415

Phe Val Asn Gly Asn Gln Pro Ile Val Thr Arg Ile Gly Ser Pro Phe
         420                 425                 430

Leu Asn Ala Pro Val Gly Gly Asn Leu Pro Ala Gly Ala Thr Ile Val
    435                 440                 445

Tyr Asp Glu Val Cys Ile Gln Ala Gly His Ile Trp Ile Gly Tyr Asn
    450                 455                 460

Ala Tyr Asn Gly Asn Arg Val Tyr Cys Pro Val Arg Thr Cys Gln Gly
465                 470                 475                 480

Val Pro Pro Asn His Ile Pro Gly Val Ala Trp Gly Val Phe Lys
             485                 490                 495

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 20
ccatggctaa gactcaagca ga                                           22

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 21
gcggccgcct atttgaatac tccccagg                                     28

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Note =
      Synthetic Construct

```
<400> SEQUENCE: 22
tccccgtgcc ggtccatcac actcaacacc acataaggcg cag                    43
```

US 8,232,370 B2

ANTIMICROBIAL PROTEIN SPECIFIC TO STAPHYLOCOCCUS AUREUS

CROSS REFERENCE TO RELATED APPLICATIONS

The present application is a National Phase Application of International Application No. PCT/KR2007/003629 filed Jul. 27, 2007, which claims priority to Korean Patent Application No. 10-2006-0073562 filed Aug. 4, 2006, which applications are incorporated herein fully by this reference.

TECHNICAL FIELD

The present invention relates to a novel antimicrobial protein having killing activity (lytic activity, antimicrobial activity) specific to *Staphylococcus aureus*.

BACKGROUND ART

A Bacteriophage is any one of a number of virus-like agents that infect bacteria and the term is commonly used in its shortened form, 'phage'. Bacteriophages consist of an outer protein hull enclosing genetic material. The genetic material can be single stranded or double stranded DNA or RNA. To survive, bacteriophages need a host and every bacterium has a specific partner phage. When the bacteriophage invades into a host, it duplicates itself and then induces expressions of enzymes involved in the decomposition of cell wall of the host cell. The enzymes destroy the cell wall by attacking murein or peptidoglycan which is responsible for rigidity and mechanical strength of the cell wall.

The bacteriophage was first found by Twort, an English bacteriologist, in 1915 during his research on the phenomenon that *micrococcus* colony is decomposed opaque by something. And in 1917, a French bacteriologist d'Herelle found out that there was something that decomposes *Shigella disentriae* in filtrate of feces of a patient with dysentery, and he continued to study to identify the material, leading to the finding of the bacteriophage which means "eating bacteria". Since then, bacteriophages had been continuously identified specific to various pathogenic bacteria including *Shigella*, typhoid *bacillus* and comma *bacillus*. Dr. Delbruck of Caltech and some European scientists who had moved to USA during World War II focused their studies on the bacteriophage specific to *E. coli*. Since penicillin was discovered by Flemming in 1950, the antibiotic has been used widely and the research on bacteriophages has been limited to some Eastern European countries. However, multi-drug resistant pathogenic bacteria have been frequently reported since 2000, which must be resulted from the abuse and misuse of antibiotics. Based on its potential for alternative antibiotics, bacteriophages have been now in the center of the studies.

Even though antibiotics (or antibacterial agents) are still major therapeutic agents for the treatment of various infectious diseases, the antibiotics-based treatment has a serious problem. Numbers of multi-drug resistant strains have been found since 1980s, and it may be due to the excessive use of such antibiotics. In 1986, *Staphylococcus aureus* having resistance against vancomycin, which is so called 'the last antibiotic', and other multi-drug resistant strains were found, giving a great shock to those in medical field. Vancomycin resistant *enterococci* (VRE) was first reported in France in 1986 and first separated in USA in 1988. Since then, the cases of *Enterococci* infection have been increased every year with high frequency, everywhere including Europe, USA, Singapore, Japan, Australia, Korea, etc, making the vancomycin resistant *Enterococci* as a causal agent of nosocomial infections. In Korea, VRE was first isolated in 1992. Therefore, it is an urgent request to develop a novel antibiotic to treat the conventional antibiotic resistant bacteria and further to lead national health and medical techniques. To achieve the above goal, a novel antibiotic has to be developed through the completely different method.

Again, it is urgently required to develop an alternative antibiotic to solve the problems of multi-drug resistant bacteria along with the abuse or misuse of the conventional antibiotics and the residual antibiotics.

Thus, the present inventors isolated a novel bacteriophage having killing activity specific to *Staphylococcus aureus* and deposited it at Korean Agricultural Culture Collection (KACC), National Institute of Agricultural Biotechnology (NIAB) on Jun. 14, 2006 (Accession No: KACC 97001P). Although this novel bacteriophage is very effective for the prevention and treatment of infectious disease caused by *Staphylococcus aureus*, the use of this bacteriophage has some defects. So, it is required to develop a novel material that improves safety of its use in various fields related to the selective killing *Staphylococcus aureus*.

The present inventors completed this invention by providing a novel antimicrobial protein having killing activity specific to *Staphylococcus aureus*, which was derived from the bacteriophage discovered by the present inventors, and further by confirming that this novel antimicrobial protein specific to *Staphylococcus aureus* can be effectively used for the prevention and treatment of disease caused by *Staphylococcus aureus*.

DISCLOSURE

Technical Problem

It is an object of the present invention to provide a novel antimicrobial protein having killing activity specific to *Staphylococcus aureus*, the causing agent of infectious diseases in human and animals.

It is another object of the present invention to provide a pharmaceutical composition for the prevention and treatment of infectious disease caused by *Staphylococcus aureus* containing the antimicrobial protein as an active ingredient.

It is a further object of the present invention to provide an antibiotic containing the antimicrobial protein as an active ingredient.

It is also an object of the present invention to provide a disinfectant containing the antimicrobial protein as an active ingredient.

Technical Solution

The present invention provides an antimicrobial protein specific to *Staphylococcus aureus* and having the amino acid sequence represented by SEQ. ID. NO: 19 and a gene encoding the same. In this description, the term 'antimicrobial activity' includes the activities resulted from lysis action and/or other antimicrobial mechanisms.

*Staphylococcus aureus* is a causing agent of skin infection and food poisoning. It is a very dangerous pathogenic bacterium having strong resistance against methicillin. It was reported that *Staphylococcus aureus* isolated in Korea had resistance against to methicillin as high as 73% at average, which is the top level in the world. That means 73% of *Staphylococcus aureus* cannot be killed by methicillin and this bacterium is highly antibiotic resistant.

The present inventors have endeavored to kill *Staphylococcus aureus* selectively. And at last, the inventors isolated *Staphylococcus aureus* from pathogen and also isolated a novel bacteriophage that is able to kill the isolated *Staphylococcus aureus* selectively. This novel bacteriophage having killing activity specific to *Staphylococcus aureus*, isolated by the inventors, was deposited at Korean Agricultural Culture Collection (KACC), National Institute of Agricultural Biotechnology (NIAB) on Jun. 14, 2006 (Accession No: KACC 97001P). The results of our research in relation to the bacteriophage were applied for a patent (Korean Patent Application No. 2006-55461).

The conventional method, which uses the bacteriophage directly, is limited in its application because of the aversion to the direct use of such a microorganism as bacteriophage. To use the bacteriophage directly, the cultivation of pathogenic host is necessary, suggesting that there might be a chance for an operator to be exposed on the pathogenic microorganism during the production of bacteriophage. Thus, strict supervision of such pathogenic bacteria is essential. To overcome the problems caused by the use of bacteriophage itself, the present inventors provide a method of producing and using a novel antimicrobial protein that is able to kill selectively *Staphylococcus aureus* by genetic engineering with a gene encoding a lytic protein of bacteriophage specific to *Staphylococcus aureus*.

The gene encoding the lytic protein of bacteriophage is expressed in the final stage of life cycle of a bacteriophage. Precisely, when the bacteriophage infects a bacterium, at the end of the multiplication cycle, the bacteriophage lytic proteins are synthesized in bacteriophage-infected cell. It is generally known that Holin, the lytic protein involved in lysis, is expressed on cell membrane inside of a bacterium, and another lysis-related lytic protein Lysin is expressed in cytoplasm of a bacterium. Holin expressed on cell membrane is transformed to make a hole on the cell membrane, through which Lysin expressed in cytoplasm is coming out with destroying a peptidoglycan layer and an outer membrane (Research in Microbiology, 153, 493-501, 2002). In this invention, an enzyme protein belonging to Lysin is used as an antimicrobial protein.

Lysin is composed of N-terminal catalytic domain and C-terminal binding domain and there is a short linker connecting these two domains. N-terminal catalytic domain has the activity of cutting 1-4 type of bridge in peptidoglycans of a bacterium. In rare cases, Lysin can have two different catalytic domains. C-terminal binding domain binds to substrate on the cell wall of target bacteria. The catalytic domain is conserved and the binding domain is variable in the same class according to the Linne's classification system. It has been generally confirmed that Lysin had equal lytic effect compared to the endogenous Lysin in a host when it is extracellularly treated. It was reported that Lysin could kill another species over its host specificity, even though it was rare (Journal of Bacteriology, 186, 4808-4812, 2004). Generally, Lysin has a more broaden bactericidal activity compared to the corresponding bacteriophage itself.

The present inventors found out a gene encoding an antimicrobial protein from the genome of the bacteriophage, with which the inventors produced and purified an antimicrobial protein utilizing molecular biological and biotechnological techniques. The antimicrobial protein has the amino acid sequence represented by SEQ. ID. NO: 19 and the gene encoding the protein has the nucleotide sequence represented by SEQ. ID. NO: 18.

The present invention also provides a pharmaceutical composition for the prevention and treatment of infectious disease caused by *Staphylococcus aureus* containing the antimicrobial protein originated from the bacteriophage as an active ingredient.

The term 'treatment' herein indicates (i) the prevention of the disease caused by *Staphylococcus aureus*; (ii) the suppression of the disease caused by *Staphylococcus aureus*; and (iii) the relief of the disease caused by *Staphylococcus aureus*.

The antimicrobial protein included in the pharmaceutical composition of the invention can kill *Staphylococcus aureus* specifically, so that it is very effective in treatment of various diseases caused by *Staphylococcus aureus*.

*Staphylococcus aureus* is the number one pathogenic bacterium to cause infectious mastitis in cattle. *Staphylococcus aureus* is found in 90% of the total dairy cows in USA and the dairy cow infected by this pathogenic bacterium in total dairy cows is estimated to be 10%. *Staphylococcus aureus* is a causing agent of acute dermatitis in human, and this acute dermatitis can be suddenly developed into sepsis taking a patient's life.

*Staphylococcus aureus* is also a causing agent of pyogenic disease, sweat odor and food poisoning. Thus, the pharmaceutical composition of the present invention can be used for the treatment of various diseases caused by *Staphylococcus aureus* such as mastitis, acute dermatitis, sepsis, pyogenic disease, food poisoning, pneumonia, osteomyelitis, impetigo, bacteremia, endocarditis and enteritis. According to a preferred embodiment of the present invention, everyday spray of the antimicrobial protein of the invention around a teat of dairy cow having mastitis could significantly reduce the symptoms of mastitis, suggesting that the antimicrobial protein of the invention is effective for the treatment of mastitis.

The pharmaceutical composition of the present invention can additionally include a pharmaceutically acceptable carrier, which is exemplified by lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, but not always limited thereto. The pharmaceutical composition of the present invention can also include a lubricant, a wetting agent, a sweetener, a flavor, an emulsifier, a suspending agent, and a preservative, in addition to the above ingredients.

The pharmaceutical composition of the present invention can be applied or sprayed on the lesion, and administered orally or parenterally (for example, intravenous, intramuscular, hypodermic, local or peritoneal injection).

The effective dosage of the pharmaceutical composition of the present invention varies from the formulation, administration pathway, age, weight and gender of animal or human with a disease caused by *Staphylococcus aureus*, severity of a disease, diet, administration frequency and pathway, excretion and sensitivity. In general, the dosage can be determined by an experienced doctor with consideration of the goal of the treatment or preventive effect. According to an exemplary embodiment of the present invention, the pharmaceutical composition of the invention contains the antimicrobial protein at the concentration of 0.005% (w/v).

The pharmaceutical composition of the present invention can be formulated as a unit dose medicine or as a medicine in multidose vehicle by mixing with a pharmaceutically acceptable carrier and/or excipient by the method well known to those in the art. The pharmaceutical formulation can be selected from a group consisting of ointments, solutions, suspensions or emulsions, extracts, powders, granules, tablets or capsules and additionally includes a dispersing agent or a stabilizing agent.

In another preferred embodiment of the present invention, the present invention provides an antibacterial agent for cosmetics and an antibiotic for medical use which contain the antimicrobial protein as an active ingredient.

*Staphylococcus aureus* is frequently found in cosmetics along with *Bacillus subtilis, E. coli* and *Pseudomonas aeruginosa*. Cosmetics use oil or water as a major ingredient, to which glycerin and sorbitol, which are carbon sources of a microorganism, and amino acid derivatives and a protein which are nitrogen sources of a microorganism, are added, suggesting that there are enough nutrition and ingredients to attract microorganisms including bacteria. In addition, the term of use of the cosmetics is comparatively long, indicating that it is in high risk of contamination by a microorganism. To prevent color changes or odor changes caused by the contamination of a microorganism, an antibacterial agent is necessarily added to cosmetics for a long shelf-life.

A synthetic antiseptic such as parabens is widely used as an additive for cosmetics, but it is potentially dangerous. Particularly, since its accumulation in breast cancer cells was detected, it has been recognized that the accumulation of such synthetic antiseptic via cosmetics might be very harmful. The American Academy of Dermatology's Committee listed the synthetic antiseptic as the number two allergen causing skin trouble. Recently what worries us is that cosmetics for children also includes such artificial synthetic antiseptic, suggesting that children are exposed on such harmful antiseptic longer and much, raising the risk seriously. Therefore, it is sincerely requested to develop a natural antiseptic.

The antimicrobial protein originated from the bacteriophage of the present invention is characterized by its high specificity to *Staphylococcus aureus*, compared with other conventional antibiotics. That is, the antimicrobial protein originated from the bacteriophage can selectively kill *Staphylococcus aureus* only without killing useful bacteria, suggesting that it is a highly valuable antibiotic that has fewer side effects. The antimicrobial protein of the present invention is effective against wider variety of *Staphylococcus aureus* than the bacteriophage itself where the protein is derived (that is, the antimicrobial protein has wider active spectrum).

The antimicrobial protein-based antibiotics, unlike the conventional antibiotics, do not induce resistance so that their life cycles are comparatively long. Most conventional antibiotics are gradually limited in use because of the increasing resistance. On the other hand, the antibiotic containing the antimicrobial protein of the invention as an active ingredient can solve the problem of the antibiotic-resistance and thus has longer life cycling. Therefore, the antibiotic containing the antimicrobial protein of the invention as an active ingredient that is able to kill *Staphylococcus aureus* selectively can be effectively used as a novel antibiotic with excellent antibacterial, bactericidal and antiseptic effects. The term 'antibiotic' is used herein as a general term for antiseptics, bactericidal agents and antibacterial agents.

In another preferred embodiment of the present invention, the invention provides a disinfectant containing the antimicrobial protein originated from the bacteriophage as an active ingredient.

The distribution of bacteria isolated from nosocomial infection has been changed over time. According to a report of NNIS (National Nosocomial Infection Surveillance System), USA, Gram-positive bacteria particularly *Staphylococcus aureus* have been increasing in number among those isolated bacteria since late 1980s, and this phenomenon is consistent with that in Korea. According to a report made in Korea, the dominant distribution is *E. coli, Pseudomonas aeruginosa*, coagulase negative *Staphylococcus* and *Staphylococcus aureus* follow in that order. But, the isolation of *Staphylococcus aureus* is increasing gradually. Korean Society for Nosocomial Infection Control (KSNIC) reported in 1996 that *Staphylococcus aureus* took 17.2% of total isolated pathogenic microorganisms and *Pseudomonas aeruginosa* (13.8%) and *E. coli* (12.3%) followed. And, 78.8% of the total *Staphylococcus aureus* isolated were confirmed to have resistance against antibiotics.

Based on the above finding, the disinfectant containing the antimicrobial protein originated from the bacteriophage of the present invention that is able to kill specifically *Staphylococcus aureus* can be effectively used as a disinfectant specifically for hospitals and public health. It is also available as a general life disinfectant, a food and kitchen disinfectant, and a stall disinfectant. Moreover, the disinfectant of the invention is not the use of bacteriophage itself, so called the microorganism, but the use of protein, which people can accept for food and cooking without aversion to it.

DESCRIPTION OF DRAWINGS

The application of the preferred embodiments of the present invention is best understood with reference to the accompanying drawings, wherein:

FIG. 1 is a set of photograph showing the result of plaque assay for detection of a bacteriophage specific to *Staphylococcus aureus*.

FIG. 2 is a schematic diagram illustrating the isolation procedure of the bacteriophage having killing activity specific to *Staphylococcus aureus*.

FIG. 3 is an electron microphotograph showing the *Staphylococcus aureus* specific bacteriophage isolated through plaque assay.

FIG. 4 is a schematic diagram illustrating the construction procedure of the genomic library of the bacteriophage and an exemplary readout for a sequencer showing SEQ ID NO: 22.

FIG. 5 is a diagram illustrating the selection of the recombinant plasmid.

FIG. 6 is a diagram showing the results of gene analysis with NCBI Blast program.

FIG. 7 is a contig map constructed using the result of gene analysis.

FIG. 8 is a diagram showing the result of open reading frame analysis using NCBI Blast and Vector NTI ContigExpress programs.

FIG. 9 is a diagram showing the result 1 of the analysis of gene encoding lytic protein by NCBI Blast program.

FIG. 10 is a diagram showing the result 2 of the analysis of gene encoding lytic protein by NCBI Blast program.

FIG. 11 is a result of protein electrophoresis showing the expressed antimicrobial protein. Lane M: size marker; Lanes 1 and 2: negative controls of Lanes 5 and 6 (in the case of not inducing expression); Lanes 3 and 4: negative controls of Lanes 7 and 8 (in the case of not inducing expression); Lanes 5 and 6: CHAP and amidase regions expressed separately, and Lanes 7 and 8: whole antimicrobial protein containing both CHAP region and amidase region.

FIG. 12 is a result of the investigation of lytic activity against two clinical isolates of *Staphylococcus aureus*. (A) and (B): two different strains of *Staphylococcus aureus*; W: whole cell lysate; P: pellet resulted from centrifugation of the cell lysate, insoluble fraction; and S: supernatant resulted from the centrifugation of the cell lysate, soluble fraction.

FIG. 13 is a result of the investigation of lytic activity against various bacteria, wherein (A) shows the lytic activity to *Staphylococcus aureus*, (B) shows the lytic activity to *Streptococcus*, (C) shows the activity to *Lactococcus lactis* and *Lactobacillus* sp. bacteria, and (D) shows the lytic activity to *E. coli* and Coliform bacteria. In (A), S1 is SAU-YH, S2 is SAU-HR1, S3 is SAU-HR2, S4 is SAU-HR3 and S5 is ATCC 31886. In (B), E.FAL is EFA-HR, E.FAC is ETC-HR, S.agal1 is ATCC 27956, S.agal2 is ATCC 7077, S.U1 is SU-HY and S.U2 is ATCC BAA-854. In (C), L.L is *Lactococcus lactis*, L.R is *Lactobacillus reuteri*, L.P is *Lactobacillus plantarum*, L.B is *Lactobacillus brevis*, and L.A is *Lactobacillus acidophilus*. In (D), E is *E. coli*, C is *Citrobacter koseri* and in each case PC indicates a positive control, NC indicates a negative control, L indicates supernatant addition after centrifugation of the cell lysate and BC indicates a buffer control.

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Isolation of *Staphylococcus aureus* from a Pathogen and Isolation of the Bacteriophage Having Killing Activity Specific to *Staphylococcus aureus*

<1-1> Isolation of *Staphylococcus aureus*

Bacteriophages generally live together with bacteria in natural system. To isolate the bacteriophage specifically infecting *Staphylococcus aureus*, samples were collected from everywhere where the inventors expected *Staphylococcus aureus* lives. To investigate the samples where *Staphylococcus aureus* really exists, the Baird-Parker agar medium, a *Staphylococcus aureus* selection medium, was used.

Particularly, the present inventors selected dairy cow mastitis as a target disease to isolate *Staphylococcus aureus*, the target microorganism. Mastitis is one of the most representative diseases caused by *Staphylococcus aureus*. A sample was taken from milk of a dairy cow with mastitis and *Staphylococcus aureus* was isolated therefrom using the Baird-Parker agar medium, a *Staphylococcus aureus* selection medium. The isolated *Staphylococcus aureus* was identified as *Staphylococcus aureus* by biochemical analysis including Gram staining method, catalase test and analysis with Vitek of bioMeriuex. The results are shown in Table 1.

TABLE 1

| Vitek ID | 200000-0 (A1-18) catalase + Coagulase+ | | | | |
|---|---|---|---|---|---|
| Type | Gram positive identification card (GPI) | | | | |
| Condition | Final | | | | |
| Time | 5 hours | | | | |
| Organism | *Staphylococcus aureus* | | | | |
| PB+ | BAC− | OPT+ | HCS+ | 6NC+ | 10B+ |
| 40B− | ESC− | ARG− | URE− | TZR+ | NOV− |
| DEX+ | LAC+ | MAN+ | RAF− | SAL− | SOR− |
| SUC+ | TRE+ | ARA− | PYR+ | PUL− | INU− |
| MEL− | MLZ− | CEL− | RIB− | XYL− | CAT+ |
| BH/CO+ | | | | | |

<1-2> Isolation of the *Staphylococcus aureus* Specific Bacteriophage

To isolate a bacteriophage specific to the isolated *Staphylococcus aureus*, samples expected to contain the bacteriophage were cultured together with *Staphylococcus aureus*. The culture broth was centrifuged, filtered and then cultured again with *Staphylococcus aureus*, the bait for the isolation of a bacteriophage, and then lysis of *Staphylococcus aureus* was investigated. The lysis was finally verified by plaque assay.

Particularly, to isolate the bacteriophage having killing activity specific to *Staphylococcus aureus*, samples were collected from soil and straw in a cowshed and sewage where the bacteriophage was expected to be. These samples were cocultivated with the previously isolated *Staphylococcus aureus* in example <1-1> at 37° C. for 3-4 hours. After cultivation, the culture broth was centrifuged for 20 minutes at 8,000 rpm. The supernatant was filtered with a 0.45 μm filter. With resultant filtrate, the *Staphylococcus aureus* specific bacteriophage was isolated by plaque assay (FIG. 1). The method used for isolation of the *Staphylococcus aureus* specific bacteriophage is shown in the schematic diagram of FIG. 2.

To observe the morphology of the obtained bacteriophage, CsCl density gradient (density: 1.15 g/ml, 1.45 g/ml, 1.50 g/ml and 1.70 g/ml) centrifugation (38,000 rpm, 22 hours, 4° C.) was performed, leading to the purification of the bacteriophage. The purified bacteriophage was loaded in a cupper grid, followed by negative staining with 2% uranyl acetate and drying. The morphology was observed under electron microscope. As a result, the isolated bacteriophage was confirmed to be the one belonging to T4-like phage genus, Myoviridae family according to the morphological classification method (FIG. 3).

EXAMPLE 2

Genetic Characteristics of the *Staphylococcus aureus* Specific Bacteriophage Isolated The gene of bacteriophage isolated was sequenced. To do so, the genome of the bacteriophage was first extracted by the conventional method and its genetic characteristics were examined.

Particularly, 200 ml of TSB (tryptic soy broth) medium (casein digest, 17 g/l; soybean digest, 3 g/l; dextrose, 2.5 g/l; NaCl, 5 g/l; dipotassium phosphate, 2.5 g/l), 50 ml of *Staphylococcus aureus* culture broth ($OD_{600}$=1) and 1 ml of filtered bacteriophage solution at the concentration of $10^8$ pfu/ml were added into a 1 l flask, followed by shaking-culture at 37° C. for 3-4 hours. Then, lysis of *Staphylococcus aureus* was observed. After confirming lysis, the culture broth was filtered with a 0.45 μm filter. After filtration, 20% polyethylene glycol 8000/2.5 M NaCl aqueous solution was added to the filtrate by the volume of ⅙ of the total volume of the filtrate, and the mixture was standing at 4° C. for overnight. Centrifugation was performed at 8,000 rpm for 20 minutes to obtain the bacteriophage pellet. The obtained bacteriophage precipitate was resuspended in 1 ml of phosphate buffer saline (PBS), to which 20% polyethylene glycol 8000/2.5 M NaCl aqueous solution was added again by the volume of ⅙ of the total volume of the resuspenssion solution. The mixture was standing at 4° C. again for one hour. One hour later, centrifugation was performed at 14,000 rpm for 10 minutes to obtain the purified bacteriophage precipitate. The precipitate was mixed with 200 μl of iodide buffer (10 mM Tris-HCl (pH 8.0), 1 mM EDTA, 4 M NaI). The mixture was standing at room temperature for 15 minutes, followed by extraction of the genome of the isolated bacteriophage by using DNeasy Tissue kit (Qiagen) and PCR purification kit (Labopass).

The genome extracted from the bacteriophage is a genomic DNA (gDNA). To analyze the gene sequence of the gDNA, the genome was treated with different restriction enzymes and fragmentation patterns by different restriction enzymes were observed. From the result, MspI was considered to be most appropriate for the construction of gDNA library. Thus, gDNA library was constructed by the conventional method using MspI-treated gene fragments. The method for the construction of gDNA library is shown in FIG. 4.

Particularly, partial digestion by a specific restriction enzyme (MspI was used herein) is essential to obtain various gene fragments. According to the previous experiments, the treatment of the genome with MspI for one minute at 30° C. is appropriate for the construction of gDNA library. Thus, the fragments of gDNA of the bacteriophage were obtained by the above partial digestion. The obtained fragments were introduced into pBluescript II SK(+) phagemid vector (Stratagene) using T4 ligase. The resultant recombinant plasmid having the fragment of the bacteriophage gene was introduced into E. coli Top10F' (Invitrogen) via electroporation, a kind of electro-transformation. The transformant with the recombinant plasmid was selected on the agar plate medium containing ampicillin supplemented with X-Gal (5-bromo-4-chloro-3-indolyl-beta-D-galactopyranoside) and isopropyl β-D-1-thiogalacto-pyranoside (IPTG) through Blue-White colony selection method. The selected single colony was inoculated into the liquid medium containing ampicillin, followed by shaking-culture for overnight. After cultivation, plasmids were extracted from the cultured cells using a plasmid purification kit (iNtRON). The extracted plasmids were electrophoresed using 0.8% agarose gel to confirm the size. Based on the size differences, a recombinant plasmid was selected. The selection procedure is shown in FIG. 5.

The selected plasmids were 51 in total and thus clones obtained were also 51. The clones were cultured again and plasmids were extracted from the cultured cells by the same manner as described above and nucleotide sequencing with the extracted plasmids as a template was performed. For the nucleotide sequencing, the common sequencing primers, M13 forward primer represented by SEQ. ID. NO: 1 and M13 reverse primer represented by SEQ. ID. NO: 2, were used. The nucleotide sequences obtained above were analyzed by using NCBI Blast program and the result is shown in FIG. 6.

Based on the analyzed nucleotide sequences of the bacteriophage, contig map was constructed to find the exact location of the analyzed nucleotide sequence on the full-length genome (FIG. 7). To understand the genetic functions of the nucleotide sequences, open reading frame (ORF) analysis was performed using NCBI Blast and Vector NTI ContigExpress programs (INFORMAX). And the results are shown in FIG. 8.

EXAMPLE 3

Cloning of the Gene Encoding the Lytic Protein

CHAP region which is a part of lytic protein involved in lysis was identified by ORF analysis in example 2 (FIG. 8). CHAP in ORF 5 and ORF 33 is known to be a region of lytic protein involved in lysis. To identify the location of the lysis-related gene on the genome, nucleotide sequence of the lysis-related gene was compared with the nucleotide sequences of bacteriophage G1 and Staphylococcus aureus bacteriophage K (GenBank accession number of the nucleotide sequence of bacteriophage G1 is AY954969, and GenBank accession number of the nucleotide sequence of Staphylococcus aureus bacteriophage K is AY176327), considering the isolated bacteriophage had a significant homology with those.

As a result, in the whole nucleotide sequence of the genome of bacteriophage G1, ORF042 comprising nucleotide (nt) 132132-132935 and ORF083 comprising nt 132935-133438 were confirmed to be the lysis-related genes. In the case of Staphylococcus aureus bacteriophage K, ORF30/32 comprising nt 27072-29435 and ORF33 comprising nt 29435-29938 in the whole nucleotide sequence of the genome of Staphylococcus aureus bacteriophage K were confirmed to be the lysis-related genes. Based on the finding that the bacteriophage G1 had the highest sequence similarity with the bacteriophage isolated in Example <1-1>, the present inventors designed and synthesized primers for the amplification of the lysis-related gene alone from the genome of the bacteriophage isolated by using the nucleotide sequence of lysis-related gene of the bacteriophage G1 (Table 2).

TABLE 2

| Primer | Nucleotide sequence |
|---|---|
| ply1-1F | SEQ. ID. NO: 3 |
| ply1-2R | SEQ. ID. NO: 4 |

PCR was performed with the above primers by using the genome extracted from the isolated bacteriophage as a template as follows; predenaturation at 95° C. for 2 minutes, denaturation at 94° C. for 30 seconds, annealing at 50° C. for 30 seconds, polymerization at 72° C. for 1 minute 20 seconds, 35 cycles from denaturation to polymerization, and final extension at 72° C. for 7 minutes. As a result, approximately 1.3 kb sized PCR product was obtained. The PCR product was purified by a conventional gel-extraction method.

The PCR product was introduced into pGEM-T easy vector (Promega) by following the manufacturer's instruction. E. coli. Top10F' was transformed with the prepared recombinant plasmid by electroporation. The resultant transformant was cultured and the plasmid was extracted from it by the conventional method. The extracted plasmid was digested with EcoRI, which proceeded to electrophoresis on agarose gel. The recombinant plasmids containing the PCR product were selected.

EXAMPLE 4

Sequence analysis of CHAP region

Figure 9:
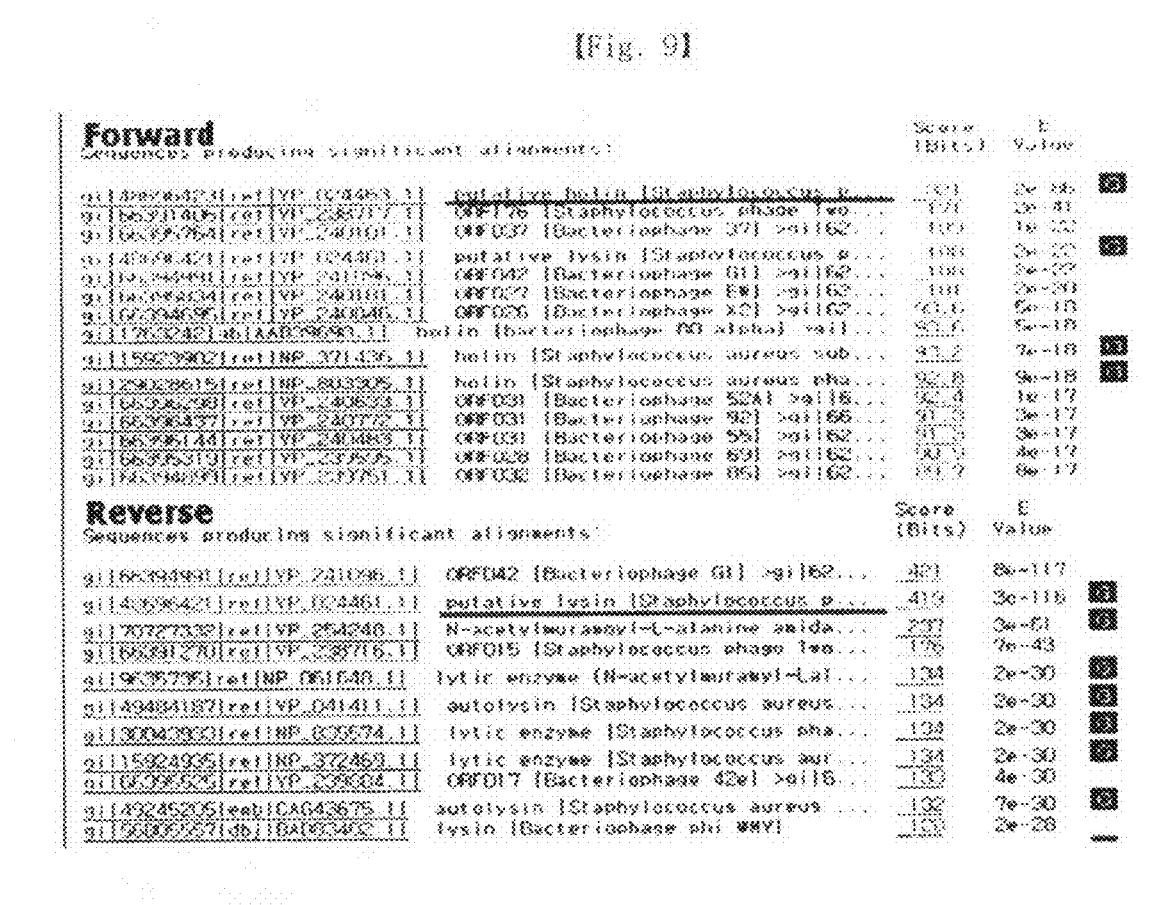

Sequencing the cloned gene in the recombinant plasmid selected in Example 4 was performed by the conventional method. M13 forward primer and M13 reverse primer were used for the sequencing. The identified sequence was further analyzed by NCBI Blast program and as a result, the cloned gene was confirmed as a part of lysis-related gene (FIG. 9). For obtaining more information about the nucleotide sequence of the gene involved in lysis, new primers were constructed, with which sequencing was performed again. These primers are shown in Table 3.

TABLE 3

| Primer | Nucleotide sequence |
|---|---|
| SEQ-1 | SEQ. ID. NO: 5 |
| SEQ-2 | SEQ. ID. NO: 6 |
| SEQ-3 | SEQ. ID. NO: 7 |

The nucleotide sequence of the gene involved in lysis (CHAP) identified from the additional sequencing was compared with the nucleotide sequence of the bacteriophage G1, which was confirmed to have the highest sequence similarity with the sequence of the bacteriophage isolated herein, by using Vector NTI AlignX (INFORMAX) program. As a result, among the identified 1,307 by sequence of the bacteriophage isolated herein, 58 bases were different from the nucleotide sequence of the bacteriophage G1. The above gene had the nucleotide sequence represented by SEQ. ID. NO: 8 and the protein translated from this gene had the amino acid sequence represented by SEQ. ID. NO: 9.

EXAMPLE 5

Analysis of the Sequence of the Full-Length Gene Encoding the Lytic Protein

The sequence identified in Example 5 corresponded to CHAP region of the lytic protein. In the bacteriophage G1 and *Staphylococcus aureus* bacteriophage K, the lytic protein is composed of CHAP region and amidase region. And the gene domains encoding these two regions were connected by intron sequence. It was assumed that an additional gene region was included in the full-length gene encoding lytic protein of the bacteriophage of the present invention, in addition to CHAP region. So, to obtain a full-length gene encoding lytic protein, additional cloning and gene sequencing were performed based on the nucleotide sequence of the CHAP region identified in Example 5. For the additional experiment, the following primers were designed and synthesized (Table 4).

TABLE 4

| Primer | Nucleotide sequence |
| --- | --- |
| Nco-Lysin F | SEQ. ID. NO: 10 |
| Not-Lysin R | SEQ. ID. NO: 11 |

PCR was performed by using the obtained genome of the isolated bacteriophage as a template with the above primers presented in Table 4 as follows: predenaturation at 95° C. for 2 minutes, denaturation at 94° C. for 30 seconds, annealing at 52° C. for 30 seconds, polymerization at 72° C. for 1 minute 20 seconds, 30 cycles from denaturation to polymerization, and final extension at 72° C. for 7 minutes. As a result, approximately 1.3 kb sized PCR product was obtained. The obtained PCR product was purified by gel-elution. The PCR product was introduced into pGEM-T easy vector (Promega) by the same manner as described in Example 4. *E. coli* Top10F' was transformed with the prepared recombinant plasmid by electroporation. The resultant transformant was cultured and the plasmid was extracted from it by the conventional method. The extracted plasmid was digested with EcoRI, which proceeded to electrophoresis on agarose gel. The recombinant plasmids containing the PCR product were selected.

Figure 10:
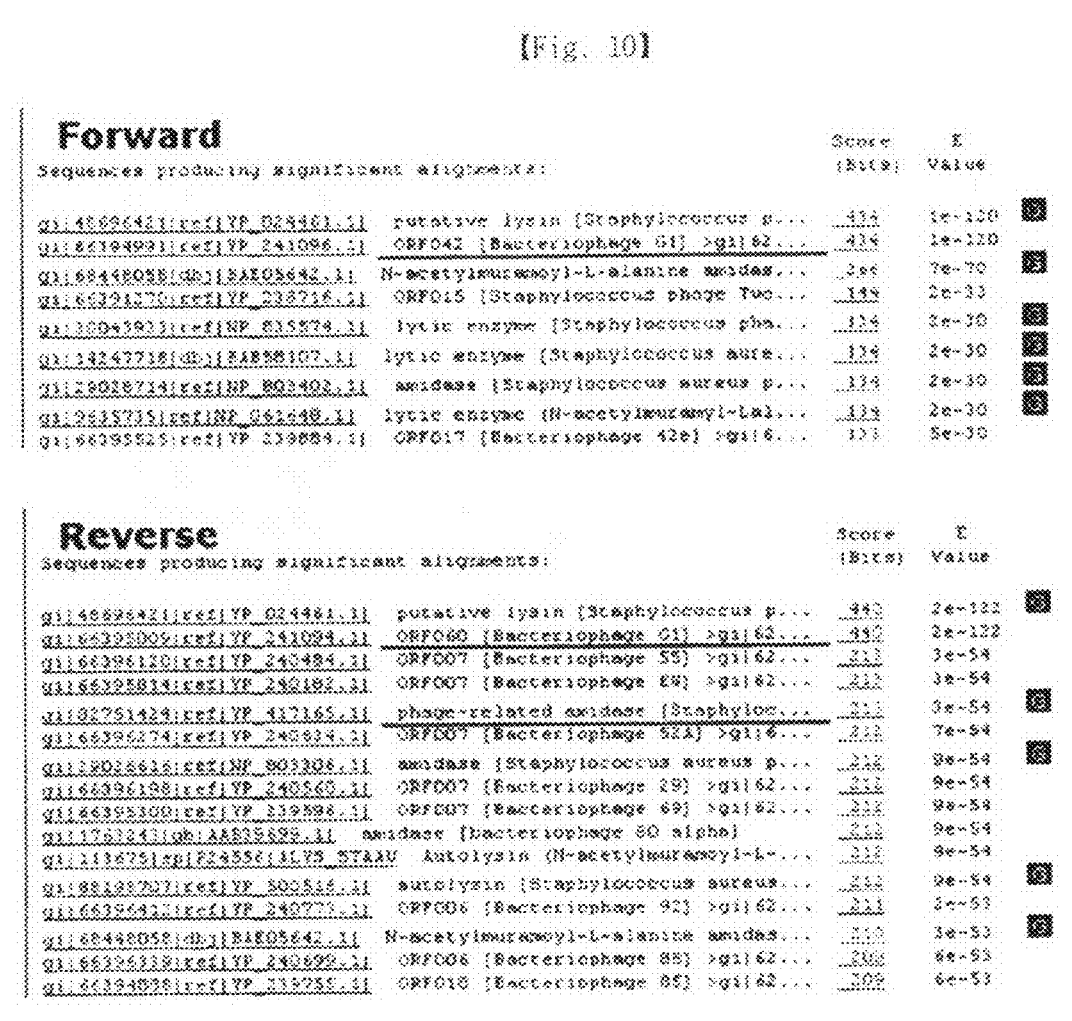

Sequencing the cloned gene in the recombinant plasmid selected was performed by the conventional method. M13 forward primer and M13 reverse primer were used for the sequencing. The identified sequence was further analyzed by NCBI Blast program and as a result, the cloned gene was identified as the gene region encoding the amidase region of the lytic protein (FIG. 10). The confirmed gene encoding amidase had the nucleotide sequence represented by SEQ. ID. NO: 12 and the protein translated from the gene had the amino acid sequence represented by SEQ. ID. NO: 13. The identified sequence was also confirmed to be one part of the full-length gene involved in lysis and encoded the amidase region.

For obtaining more information about the nucleotide sequence of the full-length gene including the CHAP and amidase regions, new primers were prepared, which are as shown in Table 5.

TABLE 5

| Primer | Nucleotide sequence |
| --- | --- |
| Lys SEQ F | SEQ. ID. NO: 14 |
| Lys SEQ R | SEQ. ID. NO: 15 |
| NLys SEQ F | SEQ. ID. NO: 16 |
| NLys SEQ R | SEQ. ID. NO: 17 |

The nucleotide sequence of the full-length gene involved in lysis identified by sequencing with the newly constructed primers was the nucleotide sequence represented by SEQ. ID. NO: 18 and the protein translated from the gene had the amino acid sequence represented by SEQ. ID. NO: 19.

EXAMPLE 6

Construction of Expression Plasmid of the Lytic Protein Involved in Lysis

To express a target antimicrobial protein including CHAP and amidase regions, pBAD-TOPO vector (Invitrogen)-based expression plasmid was constructed. PCR was performed by using the genome of the bacteriophage as a template with primers shown in Table 6.

TABLE 6

| Primer | Nucleotide sequence |
| --- | --- |
| Nco-Lysin F | SEQ. ID. NO: 20 |
| Not-Lysin R | SEQ. ID. NO: 21 |

The PCR product was digested with Nco I and Not I, and the resultant DNA fragments were obtained by the conventional gel-elution method. The DNA fragment was introduced into pBAD-TOPO vector using the Nco I and Not I cloning sites. *E. coli* BL21(DE3) was transformed with the pBAD-TOPO vector-based expression plasmid of the antimicrobial protein which was expected to have the full-length gene of antimicrobial protein.

EXAMPLE 7

Over-Expression of Antimicrobial Protein

The *E. coli* transformant constructed in the Example 7 was cultured, and then plasmid was extracted from the cultured cells by the conventional method. The extracted plasmid was digested with Nco I and Not I, and successfully cloned plasmid was selected. The antimicrobial protein was over-expressed using the transformant containing the selected plasmid. The expression system based on pBAD-TOPO vector is the L-arabinose-mediated induction system, which is favorable in the expression of toxic protein (referred to the instruction of the manufacturer under the title of "pBAD expression system" and the instruction 25-0257 published in 2004). The transformant was inoculated in a TSA medium. When the cell concentration reached 0.8-1 of $OD_{600}$, L-arabinose was added at the final concentration of 0.2% to induce the expression of an antimicrobial protein. The cells were cultured for 4 more hours from the point of induction. Then, 1 ml of the cell culture broth was taken and centrifuged at 8,000 rpm for 5 minutes to obtain cell pellet. Cell was lysed by resuspending of cell pellet in 100 μl of 1% SDS solution. 12 μl of the cell lysate was taken for electrophoresis. 3 μl of 5 (sample loading buffer was added to the cell lysate and mixed well. The gel loading sample was boiled for 5 minutes. Electrophoresis was performed with the sample by the conventional method to confirm the over-expression of an antimicrobial protein. The results are shown in FIG. 11.

In FIG. 11, lanes 5 and 6 indicate the expression of two domains of antimicrobial protein expressed separately (CHAP region: upper band; and amidase region: lower band). However, this separately expressed domain of antimicrobial protein was not effective to induce lytic activity. So, as shown in lanes 7 and 8, the expression system capable of expressing the whole antimicrobial protein containing the both CHAP and amidase regions in a single polypeptide was used for the production of the target antimicrobial protein of the invention.

EXAMPLE 8

Lytic Activity of the Expressed Antimicrobial Protein

To investigate lytic activity of the expressed antimicrobial protein, 100 μl of the culture broth of the *E. coli* transformant (conventional LB medium; 10 g/l of bacto-trypton, 5 g/l of yeast extract and 10 g/l of sodium chloride) was centrifuged at 8,000 rpm for 5 minutes and the resultant cell pellet was recovered. The cells were resuspended in 1 ml of 80 mM Tris-HCl (pH 7.6) buffer. The cells in this cell suspension were disrupted by sonication as follows; sonication was performed for 20 seconds to disrupt cells and stopped to take a break for 5 seconds, which was repeated for 20 minutes. The obtained whole cell lysate was centrifuged again (10,000×g, 5 minutes) to separate precipitate and supernatant. The antimicrobial activity in each cell lysate, precipitate and supernatant was examined. The precipitate herein includes insoluble substances in addition to cell debris, and the supernatant includes water-soluble substances. So, if the expressed antimicrobial protein is water-soluble, the activity in the supernatant will be higher. If the expressed antimicrobial protein is insoluble, the activity will be hardly detected in the supernatant or higher in the precipitate. The bacteria used for the investigation of lytic activity were two kinds of *Staphylococcus aureus*, clinically isolated by the inventors.

1 ml of *Staphylococcus aureus* culture broth, cultured in TSA medium until $OD_{600}$ was 1, was spread on agar plate and dried. 5 μl of the cell lysate, 5 μl of precipitate suspended in 20 μl of Tris-HCl buffer and 5 μl of the supernatant obtained after centrifugation of the cell lysate were dropped onto the dried medium above, followed by incubation in a 37° C. incubator for overnight. Then, the lytic activity was investigated.

As a result, the sample not expressing the antimicrobial protein did hot exhibit any lytic activity, while the sample expressing the antimicrobial protein exhibited lytic activity. The lytic activity was observed in every cell lysate, precipitate and supernatant, but among them, the lytic activity in the supernatant was the highest, suggesting that the antimicrobial protein was mostly expressed in water-soluble form (FIG. 12). In FIG. 12 (A) and (B), clear zones caused by the lytic activity of the antimicrobial protein were observed. The white circles of P of upper (A) and W, P and S of upper (B) are the round filter paper disks absorbing cell lysate, precipitate suspension and supernatant including the antimicrobial protein. As a result, in this experiment, the formation of clear zone was also confirmed around the filter paper disks even though it was weaker than that observed in the cases when cell lysate, precipitate and supernatant were directly dropped onto the medium. This weak activity was later confirmed to be attributed to small amount of the antimicrobial protein loaded on the filter paper.

The lytic activity of the antimicrobial protein against other bacteria was additionally investigated. Different bacteria were cultured by the same manner as described above and the cultured bacteria were spread on the agar plates. 5 μl of the antimicrobial protein solution (supernatant after centrifugation of the cell lysate) was dropped onto the plate, followed by incubation at 37° C. for overnight. The lytic activity of the antimicrobial protein against each bacterium was investigated. In testing against gram positive bacteria and *Staphylococcus aureus*, a solution containing lysostaphin at the concentration of 5 mg/ml, which is the compound generally used for the cell lysis, was used as a positive control. In testing against gram negative bacteria, a solution containing lysozyme at the concentration of 10 mg/ml was used as a positive control. 80 mM Tris-HCl buffer used in the preparation of cell lysate containing the antimicrobial protein above was used as a buffer control and the conventional phosphate buffered saline was used as a negative control. The total number of bacteria used for this experiment was 18 and summarized in Table 7.

TABLE 7

| Abbreviation | Origin | Bacteria |
| --- | --- | --- |
| SAU-YH | bovine mastitis | *Staphylococcus aureus* |
| SAU-HR1 | bovine mastitis | *Staphylococcus aureus* |
| SAU-HR2 | bovine mastitis | *Staphylococcus aureus* |
| SAU-HR3 | bovine mastitis | *Staphylococcus aureus* |
| ATCC 31886 | bovine mastitis | *Staphylococcus aureus* |
| E. FAL | bovine mastitis | *Enterococcus faecalis* |
| E. FAC | bovine mastitis | *Enterococcus faecium* |
| S. agal1 | bovine mastitis | *Streptococcus agalactiae* |
| S. agal2 | bovine mastitis | *Streptococcus agalactiae* |
| S. U1 | bovine mastitis | *Streptococcus uberis* |
| S. U2 | bovine mastitis | *Streptococcus uberis* |
| L. L | porcine intestine | *Lactococcus lactis* |
| L. R | porcine intestine | *Lactobacillus reuteri* |
| L. P | porcine intestine | *Lactobacillus plantarum* |
| L. B | porcine intestine | *Lactobacillus brevis* |
| L. A | porcine intestine | *Lactobacillus acidophilus* |
| E | bovine mastitis | *Escheria coli* |
| C | bovine mastitis | *Citrobacter koseri* |

The results of the investigation of lytic activity are shown in FIG. 13. As shown in FIG. 13, the antimicrobial protein of the invention had lytic activity against *Staphylococcus aureus*, while it exhibited no lytic activity against *Streptococcus* clinically separated. Besides, the antimicrobial protein of the invention did not exhibit lytic activity against any of *Lactococcus lactis* and *Lactobacillus* sp. bacteria, clinically separated *E. coli* and Coliform bacteria. Therefore, it was concluded that the antimicrobial protein of the invention had *Staphylococcus aureus* specific lytic activity.

Although the bacteriophage itself which was the origin of the antimicrobial protein of the invention had specific lytic activity against *Staphylococcus aureus* S2 alone (FIG. 13(A)), the antimicrobial protein of the invention had lytic activity against all kind of *Staphylococcus aureus* including *Staphylococcus aureus* S2, suggesting that the antimicrobial protein of the invention has wider target range than the bacteriophage itself has.

More precisely, in FIG. 13(A), clear zone was observed in a PC (positive control) and L treated with the antimicrobial protein. But in FIG. 13(B), clear zone was not observed in the PC and even worse in L treated with the antimicrobial protein and a buffer control where opaque bacteria growth spots (opaque spots) resulted from the proliferation of bacteria were observed instead of clear zone. In FIG. 13(C), opaque bacteria growth spots resulted from the proliferation of bacteria were observed instead of clear zone. In FIG. 13(D), clear zone was observed in the PC only.

EXAMPLE 9

Separation and Purification of the Expressed Lytic Protein 500 ml of the culture broth of the transformant cultivated in LB medium was centrifuged at 8,000 rpm for 5 minutes to obtain cell precipitate. The precipitate was suspended in 6 ml of 20 mM sodium phosphate buffer (pH 6.0) containing 1 mM of phenylmethylsulfonyl fluoride. To precipitate the ribosomal proteins, 2 mg of streptomycin sulfate was additionally added thereto. Cells in the suspension were disrupted by sonication by the same manner as described in Example 9. The cell lysate was centrifuged at 8,000 for 5 minutes to remove the cell debris. Ammonium sulfate (60% (w/v)) precipitation was performed with the resultant supernatant to concentrate the expressed antimicrobial protein. More precisely, ammonium sulfate was added at the final concentration of 60% (w/v) and the resultant solution was left in ice for 15 minutes to precipitate the expressed protein. 15 minutes later, the solution was centrifuged at 10,000×g for 15 minutes to recover the precipitate. The precipitate was dissolved in 2 ml of adsorption buffer (50 mM sodium phosphate, 0.25 M sodium chloride, pH 6.5) for chromatography. To remove the excessive ammonium sulfate, the prepared protein solution was dialyzed against adsorption buffer at 4° C. for overnight by replacing the adsorption buffer with a fresh buffer from time to time. Upon completion of dialysis, the protein solution was centrifuged at 10,000×g for 25 minutes to remove insoluble substances. The protein solution was then filtered with 0.2 µm filter, followed by cation-exchange chromatography. At that time, CM-Sephadex C-50 (Pharmacia) was used as the cation-exchange resin. The column was packed with the CM-Sephadex C-50 by 2×7 cm and at this time the total packed bed volume was approximately 14 ml. The column was equilibrated with the adsorption buffer before sample loading. Then, the sample containing the antimicrobial protein was loaded onto the column, followed by washing with 100 ml of the adsorption buffer. In this condition, other proteins originated from $E.\ coli$ did not adhere to the matrix of column. The antimicrobial protein was eluted by using 50 mM of sodium phosphate solution (pH 6.5) containing sodium chloride at different concentrations from 0.2 to 0.8 M. To remove sodium chloride used for the elution of the antimicrobial protein, the eluent fraction containing the antimicrobial protein was dialyzed against mM of sodium phosphate solution (pH 6.5) at 4° C. for overnight by replacing the sodium phosphate solution with fresh sodium phosphate solution from time to time. The dialysate was concentrated through performing dialysis of protein solution against polyethyleneglycol 20,000.

EXAMPLE 10

An Example of the Application of the Staphylococcus aureus Specific Antimicrobial Protein for the Prevention of Staphylococcus aureus Infection 100 µl of the supernatant obtained from centrifugation of the cell lysate containing the antimicrobial protein prepared in Example 9 was added into a 9 ml of nutrient broth (beef extract 3 g/l, peptone 5 g/l). 100 µl of the purified antimicrobial protein prepared in Example 10 was added into another 9 ml of nutrient broth. A control medium was prepared without addition of the antimicrobial protein. 100 µl of Staphylococcus aureus solution ($10^8$ cfu/ml) was added into each medium, followed by investigation of the growth of Staphylococcus aureus. In the medium not additionally treated, Staphylococcus aureus was growing so well. In the meantime, the growth of Staphylococcus aureus was not grown at all in those nutrient broths added with supernatant containing the antimicrobial protein or with the purified antimicrobial protein solution. It was confirmed from the above result that the antimicrobial proteins of the present invention prepared in Examples 9 and 10 were very effective in the prevention of the infection of Staphylococcus aureus.

EXAMPLE 11

An Example of the Application of the Staphylococcus aureus Specific Antimicrobial Protein for The Treatment of an Infectious Disease Caused by Staphylococcus aureus 15 dairy cows infected with mastitis caused by Staphylococcus aureus were selected to investigate the effect of the antimicrobial protein prepared in Example 10 on mastitis. The cows were divided into 3 groups (5 cows per group). The concentrated antimicrobial protein solution prepared in Example 10 was 100-fold diluted in 50 mM sodium phosphate solution (pH 6.5) and 10 ml of this diluted solution was sprayed on one group everyday, and 10 ml of sodium phosphate solution (pH 6.5) without the antimicrobial protein was sprayed on another group everyday, particularly on the infected regions. To a control group, 10 ml of PBS not containing the antimicrobial protein was sprayed on the infected regions everyday. The spray was continued for 10 days. As a result, significant treatment effect was observed in the group sprayed with the antimicrobial protein solution. From the result, it was confirmed that the antimicrobial protein prepared in Example 10 was very effective in the treatment of the infectious disease caused by Staphylococcus aureus.

INDUSTRIAL APPLICABILITY

As explained hereinbefore, the bacteriophage-originated antimicrobial protein of the present invention can selectively kill Staphylococcus aureus, so that it can be widely used as a preventive and therapeutic agent for infectious disease caused by Staphylococcus aureus, as an antibiotic, as an antibacterial agent for cosmetics, as a natural antiseptic, and as a multipurpose disinfectant.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The present inventors deposited the bacteriophage (Accession No: KACC97001P) at KRIBB for applying for international patent and received the Accession No: KCTC 11153BP, attached herein. The bacteriophage of Accession No: KACC 97001P is completely the same as the bacteriophage of Accession No: KCTC11153BP.

[Receipt of a Deposit of Microorganism]

The invention claimed is:

1. An isolated antimicrobial protein consisting of the amino acid sequence as set forth in SEQ. ID. NO: 19, wherein the antimicrobial protein has killing activity specific to *Staphylococcus aureus*.

2. A pharmaceutical composition comprising the bacteriophage-originated antimicrobial protein of claim 1 as an active ingredient.

3. A method of treating a disease caused by *Staphylococcus aureus* in a subject comprising administering to a subject the pharmaceutical composition of claim 2, wherein the disease is selected from the group consisting of mastitis, acute dermatitis, sepsis, pyogenic disease, food poisoning, pneumonia, osteomyelitis, impetigo, bacteremia, endocarditis and enteritis.

4. An antibiotic composition comprising the bacteriophage-originated antimicrobial protein of claim 1 as an active ingredient.

5. A disinfectant composition comprising the bacteriophage-originated antimicrobial protein of claim 1 as an active ingredient.

6. An isolated nucleic acid encoding the antimicrobial protein of SEQ. ID. NO: 19.

7. The isolated nucleic acid according to claim 6, which comprises the nucleotide sequence as set forth in SEQ. ID. NO: 18.

* * * * *